(12) United States Patent
Bene

(10) Patent No.: US 10,179,199 B2
(45) Date of Patent: Jan. 15, 2019

(54) MEDICAL APPARATUS FOR EXTRACORPOREAL BLOOD TREATMENT AND METHOD FOR DETERMINING A BLOOD PARAMETER VALUE IN A MEDICAL APPARATUS THEREOF

(71) Applicant: GAMBRO LUNDIA AB, Lund (SE)

(72) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 685 days.

(21) Appl. No.: 14/656,085

(22) Filed: Mar. 12, 2015

(65) Prior Publication Data
US 2015/0182680 A1  Jul. 2, 2015

Related U.S. Application Data

(63) Continuation of application No. 12/772,651, filed on May 3, 2010, now Pat. No. 9,002,655.

(51) Int. Cl.
*G01N 33/48* (2006.01)
*A61M 1/16* (2006.01)
*A61M 1/36* (2006.01)

(52) U.S. Cl.
CPC ............ *A61M 1/1605* (2014.02); *A61M 1/16* (2013.01); *A61M 1/1613* (2014.02);
(Continued)

(58) Field of Classification Search
None
See application file for complete search history.

(56) References Cited

U.S. PATENT DOCUMENTS

| 4,077,882 A | 3/1978 | Gangemi |
| 4,214,779 A | 7/1980 | Losell |

(Continued)

FOREIGN PATENT DOCUMENTS

| EP | 0467805 A1 | 1/1992 |
| EP | 0476192 A2 | 3/1992 |

(Continued)

OTHER PUBLICATIONS

Bretherton, S. S.; "Lecture 24: Interpolation and Smoothing", p. 1-5 referring to Daley, R., 1991: Atmospheric Data Analysis. Cambridge University Press. 457 pp.*

(Continued)

*Primary Examiner* — Larry D Riggs, II
(74) *Attorney, Agent, or Firm* — Mueting, Raasch & Gebhardt, P.A.

(57) ABSTRACT

A medical apparatus for extracorporeal blood treatment and a method for determining blood parameter value have been provided. The medical apparatus has a control unit (9) configured for taking from a storage memory (10) a plurality of blood parameter value measures each made through the sensors (8) provided on the bloodline set of each of a machines plurality at different patient treatment sessions; all the blood parameter values relate to the same patient; receiving at least a corresponding laboratory measured valise of the same blood parameter relating to the same patient and a laboratory measurement time; determining a correction factor function of a difference between a measured value made though the sensor and a laboratory measured value; obtaining an actual value of said blood parameter by varying at least the last measure made through the sensor by means of the correcting factor.

26 Claims, 11 Drawing Sheets

(52) U.S. Cl.
CPC ... *A61M 1/3609* (2014.02); *A61M 2202/0429* (2013.01); *A61M 2205/3303* (2013.01); *A61M 2205/3306* (2013.01); *A61M 2205/50* (2013.01); *A61M 2205/52* (2013.01); *A61M 2205/583* (2013.01); *A61M 2230/207* (2013.01)

(56) References Cited

U.S. PATENT DOCUMENTS

| | | | |
|---|---|---|---|
| 4,745,279 | A | 5/1988 | Karkar et al. |
| 5,158,091 | A | 10/1992 | Butterfield et al. |
| 5,291,884 | A | 3/1994 | Heinemann et al. |
| 5,331,958 | A | 7/1994 | Oppenheimer |
| 5,351,686 | A | 10/1994 | Steuer et al. |
| 5,356,593 | A | 10/1994 | Heiberger et al. |
| 5,456,253 | A | 10/1995 | Steuer et al. |
| 5,470,483 | A | 11/1995 | Bene et al. |
| 5,601,080 | A | 2/1997 | Oppenheimer |
| 5,817,007 | A | 10/1998 | Fodgaard et al. |
| 5,939,640 | A | 8/1999 | Hauser |
| 6,039,078 | A | 3/2000 | Tamari |
| 6,041,246 | A | 3/2000 | Krivitski et al. |
| 6,171,253 | B1 | 1/2001 | Bullister et al. |
| 6,246,894 | B1 | 6/2001 | Steuer et al. |
| 6,510,330 | B1 | 1/2003 | Enejder |
| 6,526,357 | B1 | 2/2003 | Soussan et al. |
| 6,542,761 | B1 | 4/2003 | Jahn et al. |
| 6,611,320 | B1 | 8/2003 | Lindberg et al. |
| 6,794,194 | B2 | 9/2004 | Fava et al. |
| 7,001,353 | B2 | 2/2006 | Bosetto et al. |
| 7,074,191 | B2 | 7/2006 | Bosetto et al. |
| 7,361,267 | B2 | 4/2008 | Delnevo |
| 7,749,184 | B2 | 7/2010 | Cavalcanti et al. |
| 8,017,407 | B2 | 9/2011 | Navon |
| 2004/0019314 | A1 | 1/2004 | Delnevo |
| 2004/0057037 | A1 | 3/2004 | Ohishi et al. |
| 2004/0073153 | A1 | 4/2004 | Bosetto |
| 2004/0144724 | A1 | 7/2004 | Bosetto et al. |
| 2007/0112289 | A1* | 5/2007 | Cavalcanti ........ A61M 1/3621 604/4.01 |
| 2009/0234289 | A1 | 9/2009 | Gagel et al. |
| 2010/0110416 | A1* | 5/2010 | Barrett ............ A61B 5/14535 356/40 |
| 2010/0113891 | A1* | 5/2010 | Barrett ............ A61B 5/14535 600/301 |

FOREIGN PATENT DOCUMENTS

| | | |
|---|---|---|
| EP | 0575712 A2 | 12/1993 |
| EP | 1078642 A2 | 2/2001 |
| EP | 1365820 A1 | 12/2003 |
| IT | 1240489 B | 12/1993 |
| JP | 60-94238 A | 5/1985 |
| JP | 62-265563 A | 11/1987 |
| JP | 63-221221 A | 9/1988 |
| JP | 4-190141 A | 7/1992 |
| JP | 9-024026 A | 1/1997 |
| JP | 9-500721 A | 1/1997 |
| JP | 11-226119 | 8/1999 |
| JP | 2000-060965 A | 2/2000 |
| JP | 2001-099735 A | 4/2001 |
| JP | 2003-508143 A | 3/2003 |
| WO | 9427495 A1 | 12/1994 |
| WO | 9504266 A1 | 2/1995 |
| WO | 0033053 A1 | 6/2000 |
| WO | 0117420 A1 | 3/2001 |
| WO | 0117421 A1 | 3/2001 |
| WO | 0145770 A1 | 6/2001 |
| WO | 02098492 A1 | 12/2002 |
| WO | 2008090406 A2 | 7/2008 |

OTHER PUBLICATIONS

Franke, R.; "Scattered Data Interpolation: Tests and Some Methods"; Mathematics of Computation, vol. 38, No. 157, Jan. 1982, p. 181-200.*

Mancini, E. et al; "Continuous On-Line Optical Absorbance Recordings of Blood Volume Changes during Hemodialysis"; Artificial Organs, 1993, 17(8):691-694.*

Bland, J. M.; et al.; "Statistical Methods for Assessing Agreement between two methods of clinical measurement"; The Lancet; vol. 327, Issue 8476, Feb. 1986; p. 307-310.*

NKF KDOQU Guidelines, "KDOQI Clinical Practice Guidelines and Clinical Practice Recommendations for Anemia in Chronic Kidney Disease", 2006, p. 1-5.

Abstract—Fishbane S., Berns JS., "Hemoglobin Cycling in Hemodialysis Patients Treated With Recombinant Human Erythropoietin", PubMed, Kidney Int., 2005, 1 page.

Abstract—Locatelli, et al., "Once-Weekly Compared with Three-Times Weekly Subcutaneous Epoetin Beta: Results From a Randomized, Multicenter, therapeutic-Equivalence Study", Pubmed, Am J. Kidney Dis., 2002, 1 page.

Abstract—Tolman, et al., "Structured Conversion from Thrice Weekly to Weekly Erythropoietic Regimens Using a Computerized Decision-Support System: A Randomized Clinical Study", Pubmed. J. Am Soc Nephrol., 2005, 1 page.

Warren, et al., "Use of 12x/Month Haemoglobin Monitoring With a Computer Algorithm Reduced Haemoglobin Variability", Nephrol Dial Transplant, 2010, Feb. 22, 2010, pp. 1-5.

NKF KDOQI Guidelines, "KDOQI Clinical Practice Guideline and Clinical Practice Recommendations for Anemia in Chronic Kidney Disease: 2007 Update of Hemoglobin Target", 2007, pp. 1-31.

NKF KDOQI Guidelines, "KDOQI Clinical Practice Guidelines and Clinical Practice Recommendations for Anemia in Chronic Kidney Disease", 2006, p. 1-7.

Nephrology Nursing Journal: EDTNA-ERCA Journal Club Discussion, "Hemolysis: A Hidden Danger", at least as early as May 2, 2010, pp. 1-10.

Moritz Friebel, et al., "Determination of Optical Properties of Human Blood in the Spectral Range 250 to 1100 nm using Monte Carlo Simulations With Hematocrit-Dependent Effective Scattering Phase Functions", Journal of Biomedical Optics, vol. 11, No. 3, May/Jun. 2006, p. 1-10.

Shiori Oshima and Yoshiyuki Sankai, "Improvement of the Accuracy in the Optical Hematocrit Measurement by Optimising Mean Optical Path Length", Artificial Organs, vol. 33, No. 9, 2009, pp. 749-756.

Trebbels, et al., "Capacitive On-Line Hematocrit Sensor Design Based on Impedance Spectroscopy for Use in Hemodialysis Machines", 31st Annual International Conference of the IEEE EMBS, Minneapolis, Minnesota, Sep. 2-6, 2009, pp. 1208-1211.

Steuer et al., "Optical Measurement of Hematocrit and Other Biological Constituents in Renal Therapy", Advances in Renal Replacement Therapy, vol. 6, No. 3 Jul. 1999, p. 217-224.

Shiori Oshima and Yoshiyuki Sankai, "Simulator With Photon and Arbitrarily Aranged RBC for Hematocrit Estimation", Proceedings of the 29th Annual International Conference of the IEEE EMBS, Lyon, France, Aug. 23-26, 2007, pp. 3623-3628.

\* cited by examiner

FIG.11

| DATE | PATIENT NUMBER | Hgb (sensor) | Hgb (LAB) | Machine number |
|---|---|---|---|---|
| 07/04/10 | 121 | 12.4 | / | 1 |
| 07/04/10 | 106 | 9.9 | 10.4 | 2 |
| 09/04/10 | 109 | 10.2 | / | 1 |
| 09/04/10 | 130 | 10.2 | / | 2 |
| 09/04/10 | 106 | 10.1 | / | 3 |
| 10/04/10 | 121 | 12.6 | / | 1 |
| 11/04/10 | 85 | 8.9 | 9.8 | 1 |
| 11/04/10 | 106 | 10.2 | / | 2 |
| 12/04/10 | 109 | / | 11.6 | / |

MEDICAL APPARATUS FOR EXTRACORPOREAL BLOOD TREATMENT AND METHOD FOR DETERMINING A BLOOD PARAMETER VALUE IN A MEDICAL APPARATUS THEREOF

TECHNICAL FIELD

The invention relates to a medical apparatus for extracorporeal blood treatment and to a method for determining a blood parameter value in a medical apparatus. The invention further relates to a method for determining an Erythropoietin Stimulating Agent (ESA) prescription, through the use of said medical apparatus.

BACKGROUND OF THE INVENTION

A dialysis machine of the known type comprises a first circuit for blood circulation, connected, when in use, to the circulatory system of a patient, a second circuit for the circulation of dialysate, and a blood treatment unit, through which the first circuit passes the blood and the second circuit passes the dialysate.

The blood treatment unit comprises a semi-permeable membrane which, when in use, separates the dialysate from the blood and permit the exchange of ions between the dialysate and the blood and the transfer of some of the blood plasma through the membrane.

The first circuit comprises a withdrawal branch located up-line from the blood treatment unit and a return branch located down-line from the blood treatment unit, while the machine comprises a peristaltic pump located in the withdrawal branch to convey the blood extracted from the patient to the blood treatment unit.

More in general, extracorporeal blood circuits are used to move blood outside the body: blood is typically pumped through tubes and arterial and venous bubble traps of disposable tubing sets connecting the patient to the blood treatment unit, for instance a dialyser mounted on the dialysis, or a treatment unit of another type (hemofilter, ultrafilter, hermodiafilter, plasmafilter, etc.) associated to a corresponding blood treatment machine.

It is also known measuring haemoglobin concentration in the blood circuit of a dialysis machine; a known way of determining the concentration of haemoglobin in the red corpuscles during the dialysis treatment (by means of high accurate measurements of an intrusive kind) requires a laboratory examination with hemolysis of blood samples taken during the dialysis session. Other dialysis machines enable non-intrusive measurements of the haemoglobin concentration to be made within the machine.

The non-intrusive measurements made within the machine are less accurate than laboratory measurements, but have the advantage of being provided in real time in such a way that the operating parameters of the dialysis machine can be corrected instantaneously.

Italian Patent IT 1240489 discloses a method of measuring the haemoglobin concentration within the machine in a non-intrusive way, by measuring the absorption of electromagnetic waves crossing the blood flowing in the withdrawal branch of the first circuit.

In order to implement this method the blood circuit having a withdrawal line, a return line and the bubble trap in the withdrawal line, also includes a calibrated and rigid piece of transparent tube rigidly engaged to the outlet of the bubble trap, upstream the connection to the dialyser.

The calibrated piece of transparent tube is designed to be received in an appropriate holder where an emitter and a receiver operate to emit and detect the absorption of electromagnetic waves.

The difference between the emitted intensity and the received intensity of the electromagnetic waves corresponds to the absorption which is correlated with the haemoglobin concentration by a specific relation.

U.S. Pat. No. 6,794,194 discloses another method for measuring the haemoglobin concentration in an extra-corporeal blood circuit of a dialysis machine comprising the measurement of the values of the blood absorption of electromagnetic waves conveyed along a section of said circuit; then the calculation of the haemoglobin concentration is made as a function of the values of absorption and the measured value of blood pressure, blood temperature and the flow rate of the blood along the aforesaid section.

According to this method the rigid piece of calibrated and transparent tube also including a pressure transducer is interposed between the blood pump and dialyser in correspondence of the withdrawal line, in a position where electromagnetic waves sensor and pressure sensor, both born by the machine, operate.

It is also known to use the measure of haemoglobin concentration as a parameter to control the fluid removal from blood.

For instance the ultrafiltration rate can be controlled by measuring the blood haemoglobin concentration upstream the treatment unit and by keeping said haemoglobin concentration or a parameter function of haemoglobin concentration (such as the filtration factor) within a range of acceptability during treatment.

EP 0467805 shows a blood treatment apparatus having an optical/electronic system comprising a LED diode and a photo sensitive sensor capable of receiving the light radiation emitted by the LED and of providing a corresponding electrical signal.

A circuit for processing this electrical signal is able to discriminate when in use whether a tube through which blood flows is placed between LED diode and the sensor.

Finally document WO 2008/90406 discloses an improved rigid tubular transparent element for further improving accuracy of the sensor provided for measuring the hematocrit concentration in the blood.

Moreover it is also known the use of erythropoietin stimulating agents (ESA) which requires a continuous monitoring of the haemoglobin rate in the patient. In the hemodialysis field, the haemoglobin recommended concentration should be comprised between 11 and 13 g/dl.

Generally in the dialysis centres, the monitor of the haemoglobin concentration is made through laboratory tests on blood withdraws from the patient once per month or, in rare cases, once every two weeks.

It is clear that during this time intervals, the haemoglobin value might move from the desired value outside the recommended range.

In this respect a mere frequent analysis of the blood sampled from the patient or a very time consuming specific analysis made by the nephorologist on the haemoglobin variation of each and every single patient can possibly reduce undesired haemoglobin oscillations.

SUMMARY

It is an object of the present invention to make available a medical apparatus capable of allowing a reliable measure of a blood parameter value, in particular using sensors already available in the treatment machines.

It is a further object of the invention to provide a medical apparatus capable of allowing a correct prescription of drugs for keeping said blood parameter within the desired range.

A further object of the invention is to make available a method for reliably determining the blood parameter value and/or also for providing a method allowing prescription of erythropoietin stimulating agents in order to adjust haemoglobin value in patients suffering from renal failure.

At least one or more of the above mentioned objects are achieved by a medical apparatus and by a method for determining a blood parameter value according to one or more of the appended claims.

According to the present invention, the medical apparatus comprises a prefixed number of machines for extraeorporeal blood treatment each having at least blood treatment unit, an extraeorporeal blood line having a withdrawal branch adapted to withdraw blood from a patient access and to bring the withdrawn blood to the blood treatment unit and return branch adapted to bring the blood from the blood treatment unit to the patient; at least one sensor associated to the extracorporeal line and adapted to provide a measure related to a blood parameter value in the blood circulating in the extracorporeal blood line; a control unit; at least one storage memory for storing measures related to the blood parameter value each made through one of the sensors of said prefixed number of machines and corresponding to different treatment session of patients on said prefixed number of machines; the control unit being configured for performing the following steps: taking from the storage memory a plurality of measures each made through one of the sensor of said prefixed number of machines at different patient treatment sessions and relating to the same patient; receiving at least an actual control value of the same blood parameter at a monitoring time relating to the same patient; determining a correcting factor function of a difference between a prefixed number of measures made through the sensors and the actual control blood parameter value for obtaining a value of said blood parameter by varying at least the last measure made through the sensor by means of the correcting factor.

According to further features of the invention, the control unit is configured for performing one or more of the following steps:
  interpolating the plurality of measures made through the sensor for obtaining a blood parameter trend along time defining an interpolated curve;
  determining the correcting factor as a difference between the laboratory measured blood parameter value and the time-corresponding value of the blood parameter in the interpolated curve;
  translating at least the last part of the interpolated curve by means of the correcting factor, the last part of the interpolated curve comprising at least the last two measured blood parameter values;
  displaying either the translated interpolated curve or the translated blood parameter values;
  determining a future trend of the interpolated curve or a future trend of the translated interpolated curve for predicting blood parameter variation after a predetermine time interval;
  determining an erythropoietin stimulating agent prescription as a function of a predicted blood parameter variation in order to maintain the hemoglobin value within a range of established hemoglobin values;
  validating the first stable measured blood parameter value in a single treatment session;
  storing said validated measure in the storage memory together with a time information and a patient identification data.

According to some specific embodiments, the medical apparatus of the invention also has a sensor configured to provide a measure relating to a blood parameter value which depends on the blood characteristic of the specific patient; according to a further characteristic of the invention, the sensor measures a blood characteristic different and only related to the blood parameter.

The apparatus may also include one or more of the following features:
  an hematocrit sensor;
  a sensor comprising an emitter of a signal and a receiver of a signal, the emitted ondulatory signal crossing at least part of the extracorporeal blood line and being partly absorbed and partly scattered by the blood inside the extracorporeal blood line;
  a processor determining the blood parameter value as a function of the received signal;
  the sensor comprising at least one mirror placed between the emitter and the receiver and outside the extracorporeal blood line for reflecting at least the scattered part of the signal.

According to the invention a method for determining a blood parameter value in the above mentioned medical apparatus comprises the step of taking from the storage memory a plurality of measures each made through one of the sensors of the prefixed number of machines at different patient treatment sessions at different times; receiving at least a laboratory measured value of the same blood parameter at a laboratory measurement time relating to the same patient; determining a correcting factor function of difference between a prefixed number of measures made through sensor and the laboratory measured blood parameter value; obtaining a value of said blood parameter by varying at least the last measure made through the sensor by means of the correcting factor. Finally the invention concerns a medical apparatus and a method for determining an actual hemoglobin value and for determining an erythropoietin stimulating agent prescription for controlling the hemoglobin concentration in the treated patient.

SHORT DESCRIPTION OF THE DRAWINGS

Further features and advantages will be better understood from the detailed description of some non limiting embodiments of the present invention.

This description will be carried out hereinafter with reference to the accompanying drawings, also given by way of non-limiting example, in which:
  FIG. 1 is a first embodiment of a medical apparatus for determining blood parameter value;
  FIG. 2 is second embodiment of a medical apparatus tor determining blood parameter value;
  FIG. 3 is a schematic view of a machine for extracorporeal blood treatment;
  FIGS. 4a and 4b show a rigid tubular element to be used with a sensor in the machine of FIG. 3;
  FIG. 5 shows a holder mounted on the machine on FIG. 3 including a sensor for the measure of a blood parameter;
  FIG. 6 is a flowchart showing the steps in a method for determining a blood parameter value using the medical apparatus shown in FIGS. 1 and 2;

FIG. 7 is a flowchart of a validating process in the apparatus according to FIG. 1 and 2;

FIG. 8 schematically shows a diagram of measured hemoglobin values and calculated actual hemoglobin values along time;

FIG. 11 shows an example of data contained in a storage memory of the medical apparatus of FIGS. 1 and 2.

DETAILED DESCRIPTION

With reference to the enclosed drawings, reference number 1 denotes a medical apparatus for an extracorporeal fluid treatment. In particular the apparatus may comprise a prefixed number of machines 2 for the treatment of blood, such as by way of non-limiting example a machine for the treatment of renal or liver insufficiency. In the example shown in the attached figures, the medical apparatus 1 presents at least one machine for one or more of the following extracorporeal blood treatments: hemodialysis, hemofiltration, ultrafiltration, hemodiafiltration, and plasmaapheresis.

Figure 1:
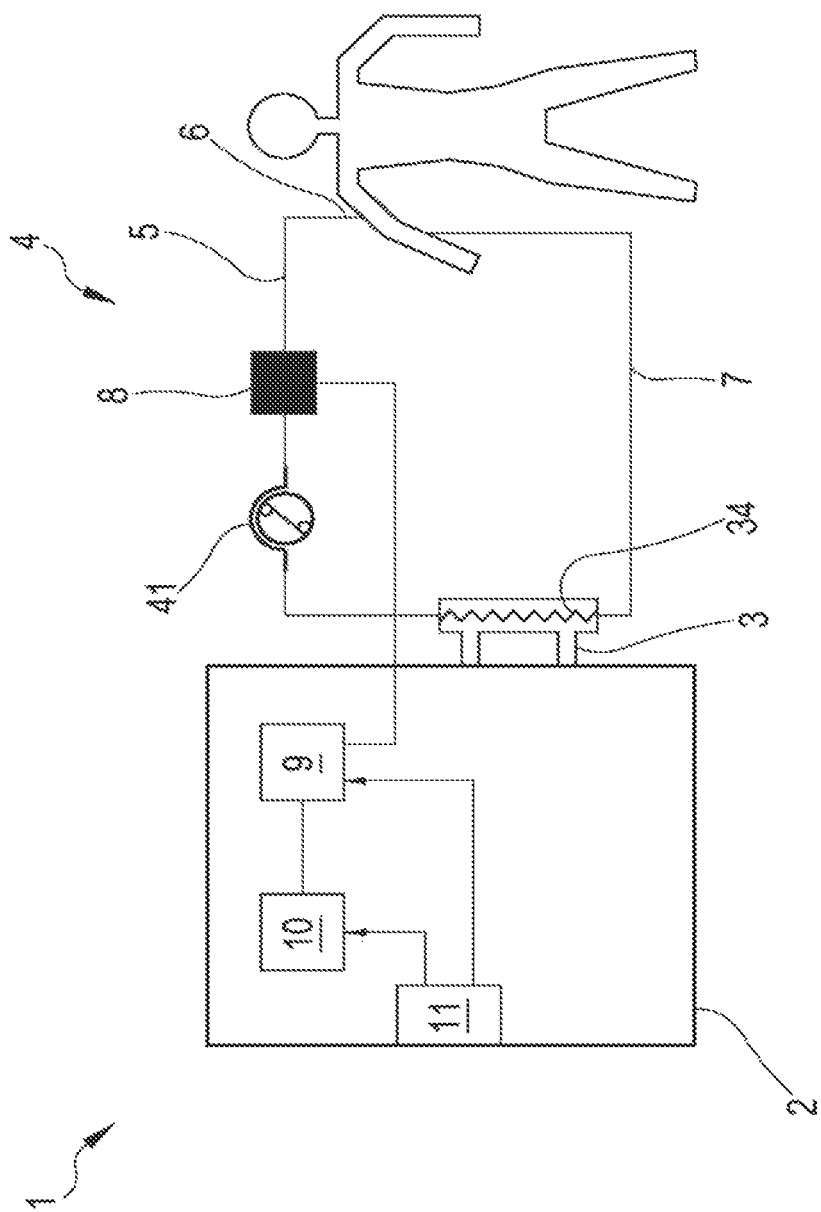
Figure 2:
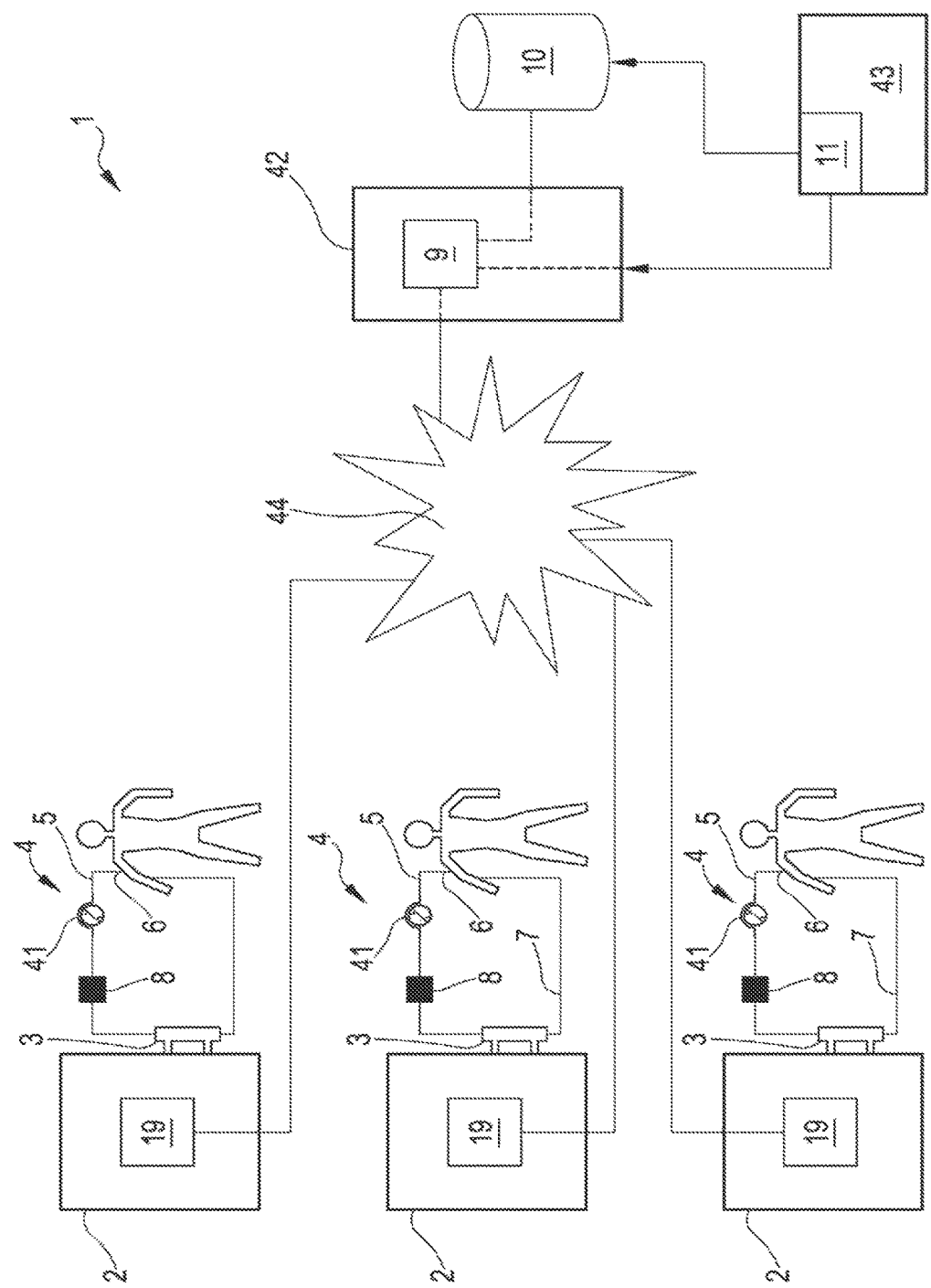

It is clear that a medical apparatus 1 having a prefixed number of medical machines 2 for extracorporeal blood treatment both includes the first embodiment according to FIG. 1 in which only one machine is shown, as well as the embodiment disclosed in FIG. 2 in which a plurality of machines (from 2 to any desired number) are used in a network 44.

Figure 3:
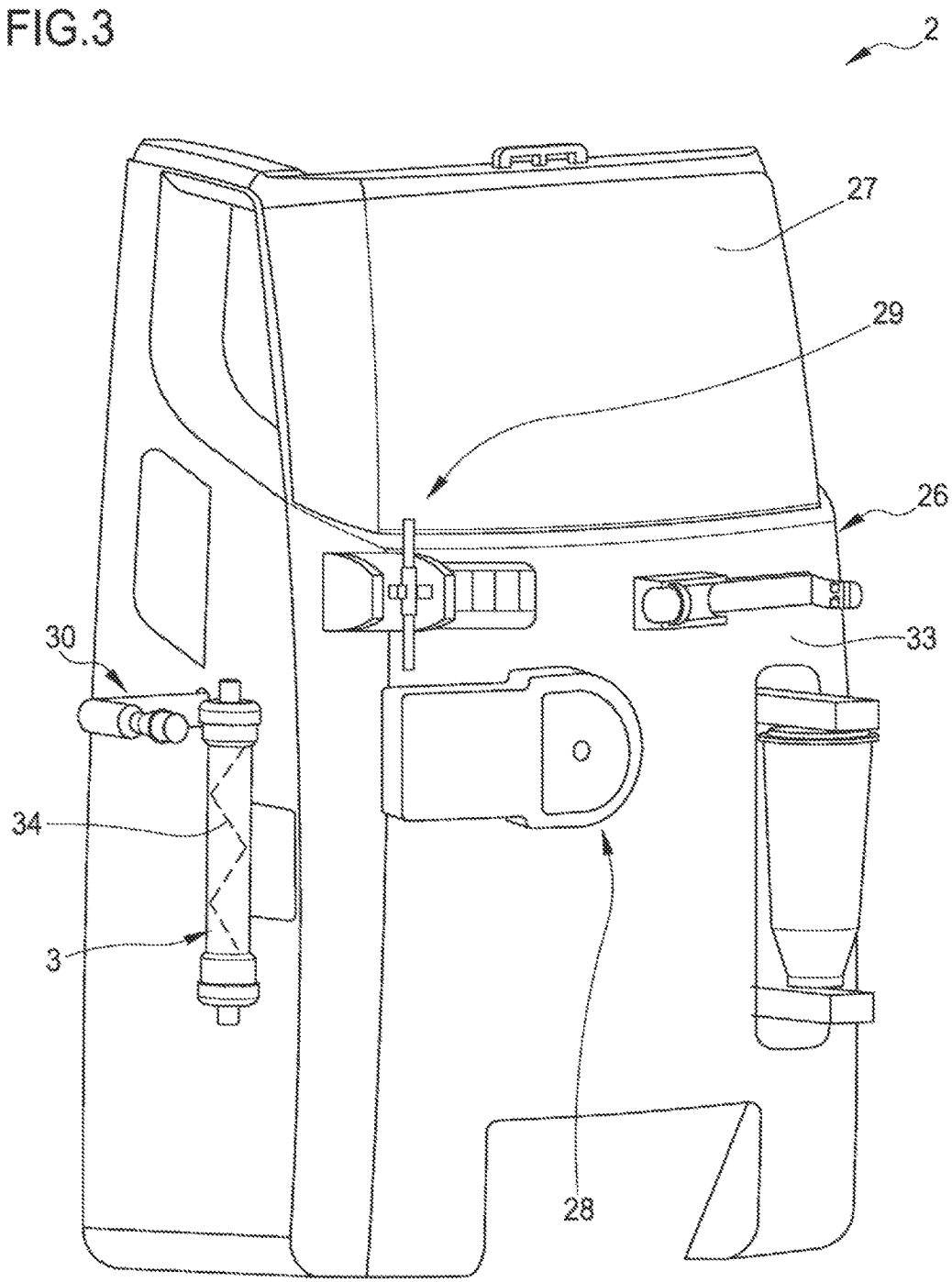

In any case, as shown in FIG. 3, each of the machine 2 (schematically shown also in FIGS. 1 and 2) may comprise a main support structure 26 and an operating panel 33, which may be in a front position of the apparatus, including a user interface 27 (only schematically represented), one or more pumps 28 (volumetric pumps of the type acting in deformation of deformable tube portions, such as peristaltic pumps), and at least a holder 29 so constructed as to receive a rigid tubular element 20 to be subject to a non invasive measurement as it will be explained in detail herein below.

The apparatus may also present an auxiliary holder 30 for receiving at least a blood treatment unit 3 (for instance a dialyzer or an ultrafilter or an hemofilter or an hemodiafilter or a plasmafilter). The blood treatment unit may comprise, in a manner per se known and therefore not further detailed, a first and a second compartment separated by a semipermeable membrane 34. The first compartment is for the passage of blood and the second compartment is for the passage of discarded substances and/or treatment liquid.

As shown in FIGS. 1 and 2 each machine 2 has an extracorporeal blood line 4 with a withdrawal branch 5 adapted to withdraw blood from a patient access 6 and to bring the withdrawn blood to the blood treatment unit 3.

A blood pump 41 (such as a peristaltic pump) may be used to generate the blood flow outside the patient body.

The extracorporeal blood line 4 also includes a return branch 7 adapted to bring the blood from the blood treatment unit 3 to the patient.

Other circuital elements could be present in the bloodline 4 but they are not shown: bubble traps on the withdrawal branch 5 and/or the return branch 7, as well as infusion lines for infusing substitution fluid and/or pressure sensors, clamps, and anticoagulant infusion device.

As can be seen from the annexed drawings, the machine 2 also include at least one sensor 8 placed in correspondence of the extracorporeal line 4 and adapted to provide a measure related to a blood parameter value in the blood circulating in the extracorporeal blood line 4.

In particular the sensor 8 may be positioned on the withdrawal branch 5 either upstream fee blood pump 41 (FIG. 1) or downstream the blood pump 41 (FIG. 2).

As above stated the mentioned sensor 8 is capable of providing a measure which is correlated to a blood parameter value which is wished to be known daring the treatment (dialysis session).

In general terms the sensor 8 may be used for measuring a blood characteristic different and only related to me blood parameter.

In other words the sensor 8 is not capable of outputting a precise and actual value of the blood parameter, but only a value which is related to the absolute value of the parameter.

In the example hereinafter disclosed, said sensor 8 may be an hematocrit sensor or a blood volume sensor. The hematocrit (Ht) is the proportion of blood volume which is occupied by red blood cells.

By contrast the blood parameter may be the hemoglobin concentration. The hemoglobin (Hb or Hgb) is the iron-containing oxygen-transport metalloprotein in the red blood cells of the blood.

As can be clearly understood, hematocrit and hemoglobin are strictly correlated but different.

Moreover, even if the hematocrit and the hemoglobin concentration are correlated, it is possible to directly convert the sensor signal into a value representative of the hemoglobin, for example through a conversion table or function, experimentally calculated.

Anyway, also in such a situation the outputted value is only related to the real hemoglobin concentration for the reasons here-below presented.

Mentioned sensor 8 generally comprises an emitter 17 of an ondulatory signal and the receiver 18 of the ondulatory signal.

The emitted signal crosses at least part of the extracorporeal blood line and is partly absorbed and partly scattered by the blood inside the extracorporeal blood line.

In greater detail, the emitter may comprise a waves emitter 17 emitting electromagnetic or acoustic waves with specified emission property (e.g. specified intensity or frequency) and the receiver 18 may comprise a detector of electromagnetic or acoustic waves which can detect a received intensity or frequency or phase.

The proposed non-limiting embodiments include in particular an optical sensor working in the visible or infrared spectrum.

A control unit 19 connected to the sensor 8 includes means for calculating a property of a fluid circulating through the rigid tubular element based on said emission and received intensities or on the phase shift between the emitted and received signals or on alteration of the frequency between emitted and received signal.

In the embodiment now described, the means for calculating a property of a fluid circulating through the rigid tubular piece can include:

means for calculating a difference or a ratio between the emission intensity and the received intensity, means for determining an absorption of energy by the fluid circulating through the rigid tubular piece based on said difference or on said ratio, means tor determining the property of the fluid circulating through the rigid tubular piece based on said absorption.

In general terms the property of the fluid circulating through the rigid tubular piece includes at least one selected in the group comprising:
blood density,
blood hematocrit,
blood hemoglobin concentration,
mean blood cellular volume.

The emitter and receiver 17, 18 may cooperate with a rigid tubular element 20 (in part transparent to said acoustic or electromagnetic waves) of the blood line 4 in particular interposed between two consecutive (possibly flexible) tubings 21, 22 of the withdrawal branch 5.

Figure 5:
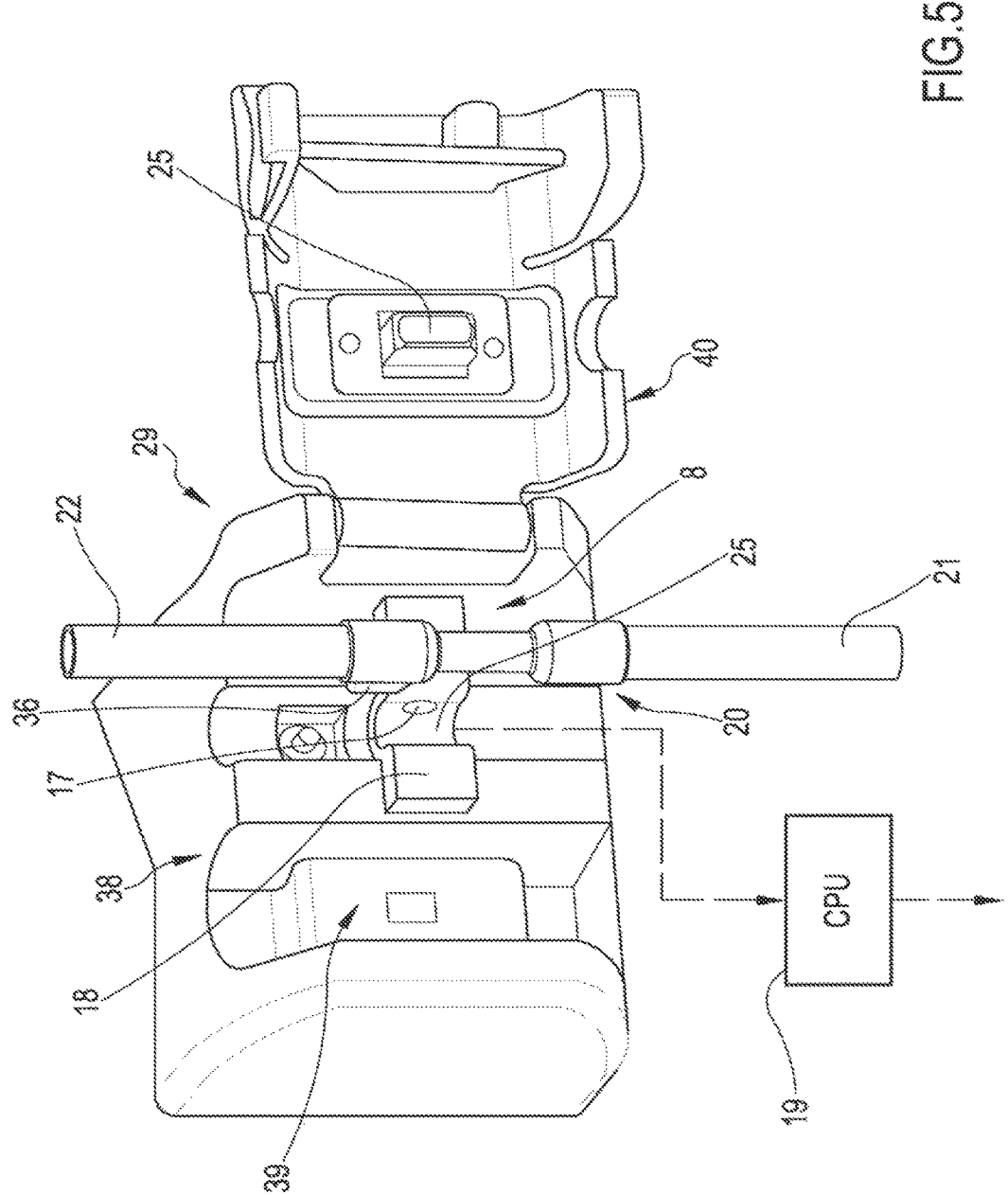

It is also to be noted that sensor 8 may farther include at least one mirror 25 (see FIG. 5) placed between the emitter 17, a receiver 18 and outside the extracorporeal blood line 4 (in particular substantially around the tube constituting the blood line 4), for reflecting at least the scattered portion of the emitted signal.

Figure 4B:
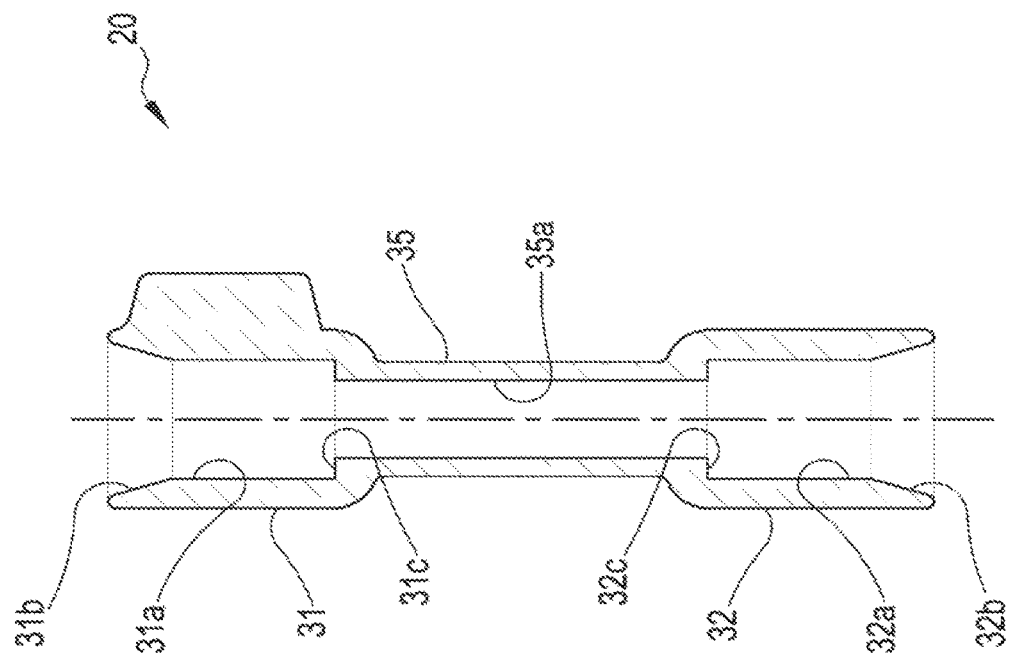
Figure 4A:
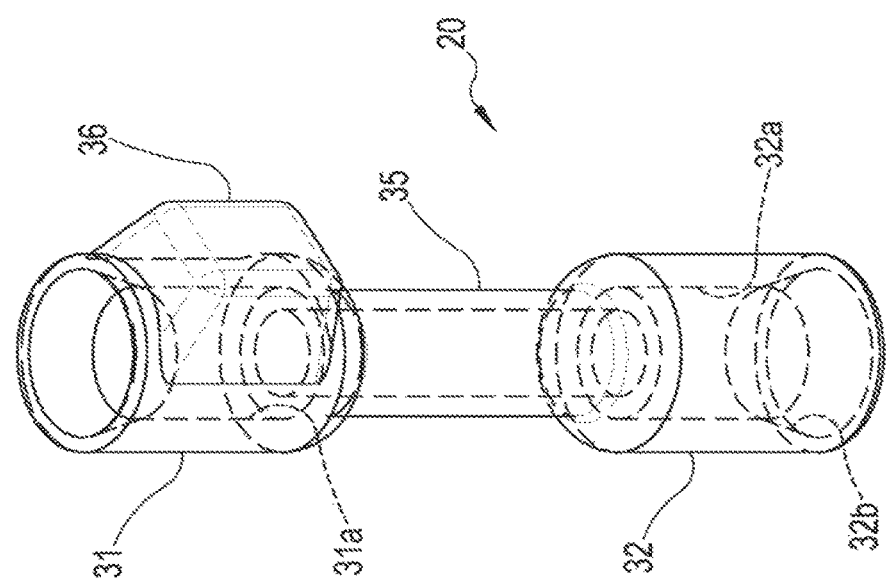

The above mentioned rigid tubular element 20 (see FIGS. 4a and 4b) has a first end connector 31, a second end connector 32 opposite said first end connector 31, and an intermediate portion 35 extending between said first and second end connectors 31, 32. The intermediate portion 35 may be designed and calibrated because in use, when it is flown through by blood, it is adopted for subjecting the fluid flowing through said intermediate portion 35 to non-invasive measurement of the blood parameter. The intermediate portion 35 may have a constant cross section and may be made of at least partially transparent material. Of course the cross section could also be variable but this may entail a more complex measurement procedure. In term of shape, again referring to the embodiment shown, the intermediate portion 35 can have a toric cross section. In the embodiment shown the rigid tubular element 20 is in a single piece made in transparent plastic material, for instance PVC (of course other rigid plastic materials can alternatively be used).

The first and second cod connectors 31, 32 may have an external prismatic, for instance cylindrical, surface and an internal prismatic surface; the internal prismatic surface of each end connector in the embodiments shown presents a main cylindrical tract 31a, 32a and a frustum-conical leading edge 31b, 32b. The cylindrical tracts have a diameter greater than that of the intermediate portion inner surface 35a in order to define an abutment 31c, 32c for the connection of the tube end portions. Notice that the intermediate portion 35 internal surface 35a can be prismatic, and in this case is cylindrical, and extends in immediate prosecution of the abutment. In practice in order to avoid stagnation areas, the diameter of the cylindrical tracts 31a, 32a can be made equal to that of the intermediate portion inner surface 35a plus two times the thickness of the end portions of the tube secured in correspondence of said end connectors. This assures that in use a continuous and smooth channel is created through the whole rigid tubular piece.

The external prismatic surface of at least one of said end connectors may bear a radially protruding element 36 which is designed to cooperate in use with a corresponding mating recess 37 provided on the holder 29 of the medical apparatus.

Going now back to the overall apparatus, machine 2 of the enclosed figures may comprise as mentioned, the holder 29 for the rigid tubular element 20. This holder may include a base 38 carried by the support structure and defining a seat 39 for receiving at least the rigid tubular element 20, and the sensor 8 associated to the base and comprising the emitter 17 and the receiver 18 which can detect a return signal. The rigid tubular element may have at least the intermediate portion 35 which is transparent or at least partially transparent to said signals in order to allow a non invasive measurement made taking into account the influence of the fluid on said signals.

The holder may also comprise a closure element 40 which is coupled to the base and which can be moved between a closed position, where it closes the seat and secures in position the rigid tubular piece, and an open position, where the closure element leaves the seat open thereby allowing insertion or removal of the tubular piece into or front the seat.

In the described embodiment, sensor 8 makes use of optical measurement capability for determining a measure related to the blood parameter.

In general the following equations show the mathematical formulation and variables involved in photo-optic determination of biologic constituent.

$$I=Ae^{\alpha d}/(e^{2\alpha d}-1)$$

When the sample thickness, d, or fee attenuation of light by the media is large, $\alpha d>1$, I, the intensity of received light, becomes $$I=Ae^{-\alpha d}$$

Where A is a complex, function of $\alpha$, S, k and $\alpha=(3K[K+S])^{1/2}$ the bulk attenuation coefficient
K=the bulk absorption coefficient
S=the bulk scattering coefficient
In whole blood $$K=(H/V)(\sigma_{ao}\text{Sat}+\sigma_{ar}[1-\text{Sat}])+(1-H)K_p \quad (4)$$

$$S=H(1-H)\sigma_s \quad (5)$$

Where $\sigma_{ar}$ and $\sigma_s$ are known red cells coefficient at given wavelengths, and at Sat is the oxygen saturation, H=hematocrit, V=mean red blood cell volume, and K=absorption coefficient of plasma.

Analites that resides in the plasma will affect either $K_p$ or $\sigma_s$.

In general the mentioned coefficient and in particular $\alpha$, is function of both scattering, as well as, absorption.

In implementing the present apparatus and present method, it was understood that absorption and mainly scattering effect are different from patient to patient due to differences in the blood corpuscles number and shapes.

In other terms two patients having the same hematocrit or the same hemoglobin concentration obtain different measurement of the same parameter (hematocrit or hemoglobin) using the non-invasive optical sensor above mentioned.

Indeed the intensity received by the receiver detecting a signal differs (even in case of identical hematocrit/hemoglobin concentration) due to the above mentioned physical differencies.

In other terms even though variations in hematocrit or hemoglobin concentration of the blood measured through sensor 8 are reliable, the absolute value of the hemoglobin concentration of a patient is only correlated, but not equal (unless rare situations) to the value measured by the sensor 8.

More in general the sensor 8 is configured to provide a measure related to a blood parameter value, depending on the blood characteristic of the specific patient under treatment.

The sensor 8 provides different blood parameter value measures for different patients having an actual blood parameter value identical one other.

Coming back to the embodiments of FIGS. 1 and 2, the medical apparatus comprises at least a control unit 9.

The control unit 9 which could be any kind of microprocessors or calculating unit, could be the one inside machine 2 (see for example FIG. 1) or a control unit 9 of an external server 42 (see FIG. 2).

The medical apparatus also includes one storage memory 10 for storing at least measures related to the blood parameter value; each measure is made through one of the sensor 8 of said prefixed number of machines 2 and corresponds to different treatment sessions of the various patients on the machines 2.

Again the storage memory 10 could be included in the machine 2 (see FIG. 1) or in an external database connected to server 42 (as in FIG. 2).

Of course any kind of database accessible to the control unit 9 is to be considered comprised in the present invention (for example a database spread on different physical media).

The medical apparatus may also include an input device 11 for providing the control unit 9 with at least an actual control value of the same blood parameter. Again the input device 11 could be directly implemented in the machine 2 (see FIG. 1) and in this respect could be coincident (or not) with user interface 27 disclosed in FIG. 3.

Alternatively the input device 11 could be directly associated with server 42.

In particular the input device 11 is used to forward to the control unit 9 an actual control value of the blood parameter.

The actual control value is a real absolute value of the blood parameter measured through reliable techniques, such as a laboratory measurements.

If the blood parameter is the hemoglobin concentration, the laboratory can obtain such a measurement by taking a patient sample and, with a standard procedure, causing blood haemolysis obtaining the cited reliable actual control value.

In this respect the input device 11 could be not only a manual input but also an automatic input device.

For example a remote processing unit 43 having the actual control value available (previously inputted by an operator or directly calculated in the analysis process) can send this value either to the control unit 9, upon request, or to the storage memory 10.

During each dialysis session of a patient on a machine 2, sensor 8 is active for measuring the blood parameter at time intervals (for example every 10 min.) during the treatment sessions.

Figure 9:
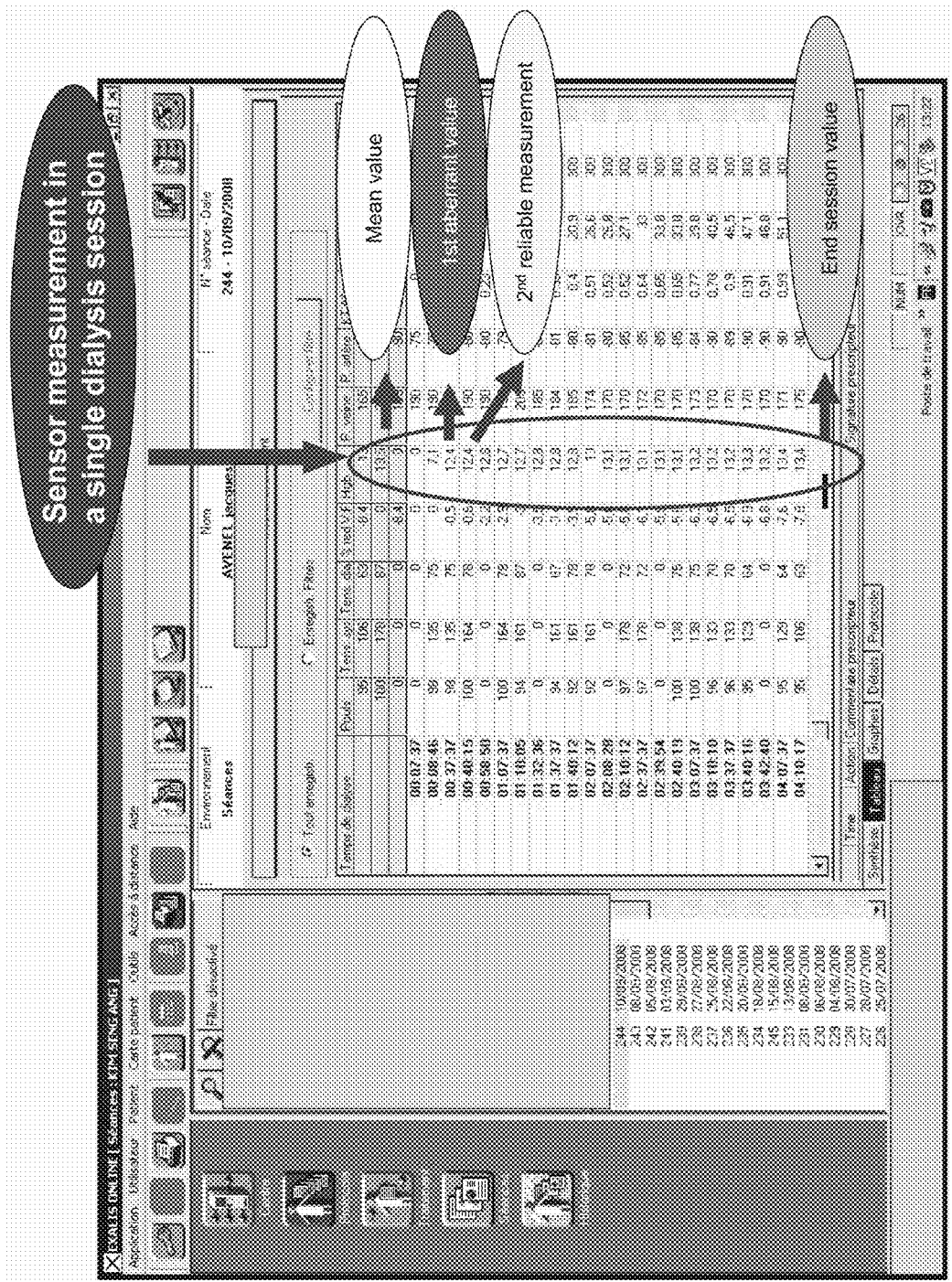
FIG. 9 shows a medical apparatus screenshot.
Figure 10:
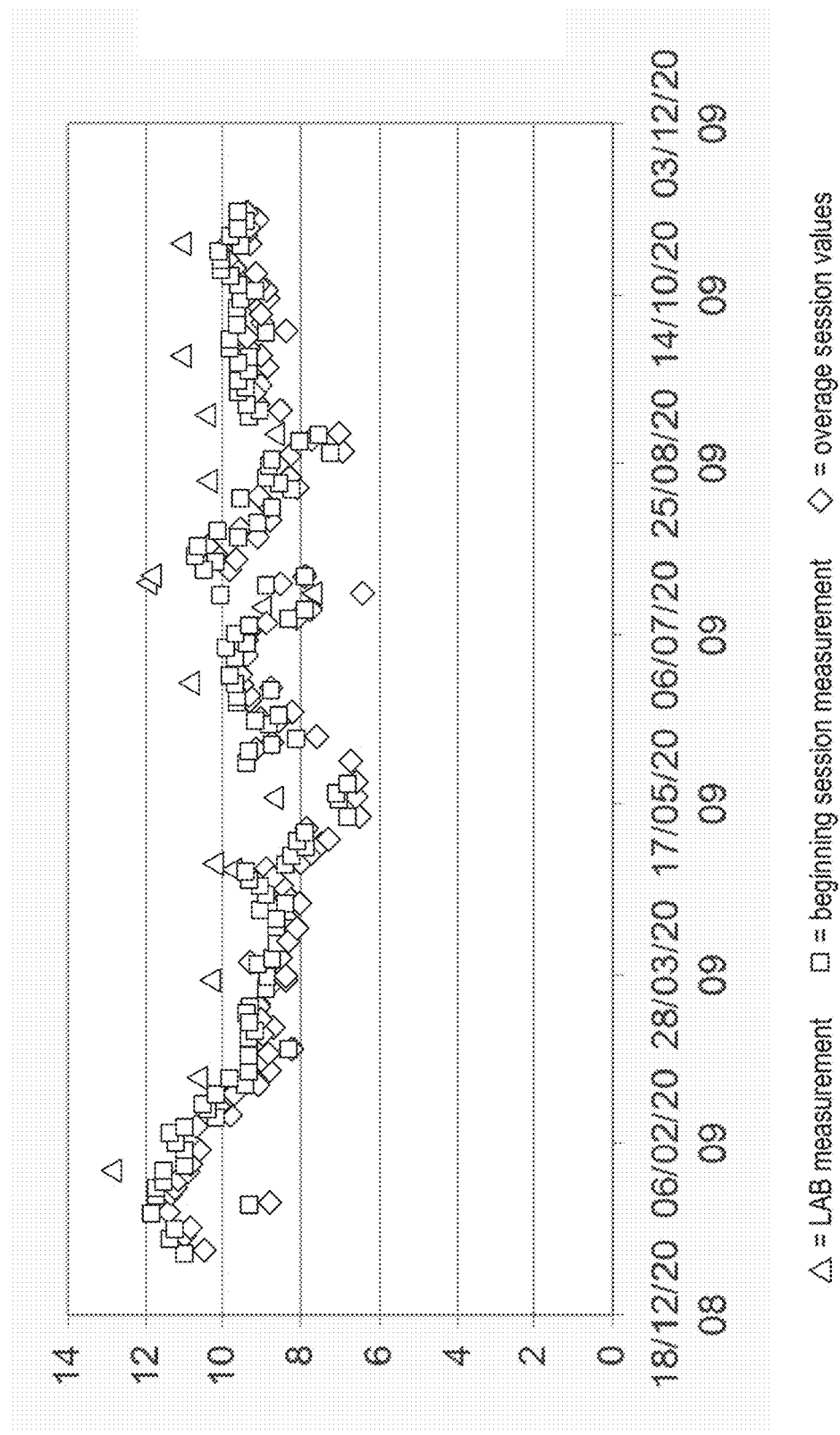
FIG. 10 shows a diagram of hemoglobin along time highlighting laboratory measurements, average session values of measured hemoglobin and pre-dialytic session of measured hemoglobin.

FIG. 9 illustrates a display printout (screenshot) of a single dialysis session on a patient including in column named "Hgb" the measures made by sensor 8 of the value correlated to the hemoglobin concentration.

As above stated such values are only to be considered related to the real hemoglobin values.

As can be seen at the beginning of the dialysis session (pre-dialytic session), aberrant values are displayed and, at certain time, particularly when the flows in the machine become constant and transitory effect on the various blood parameter comes to an end, the sensor measurements become reliable.

The control, unit is programmed for storing in the storage memory 10 at least the first reliable pre-dialytic blood parameter measurement. Generally the control unit may be configured and programmed for validating the first stable blood parameter value for each single treatment session of the patient The validated first stable measure blood parameter value may be then stored in the storage memory 10 together with at least a time information (session date or time) and a patient identification data (reference number, name, . . . ).

Figure 7:
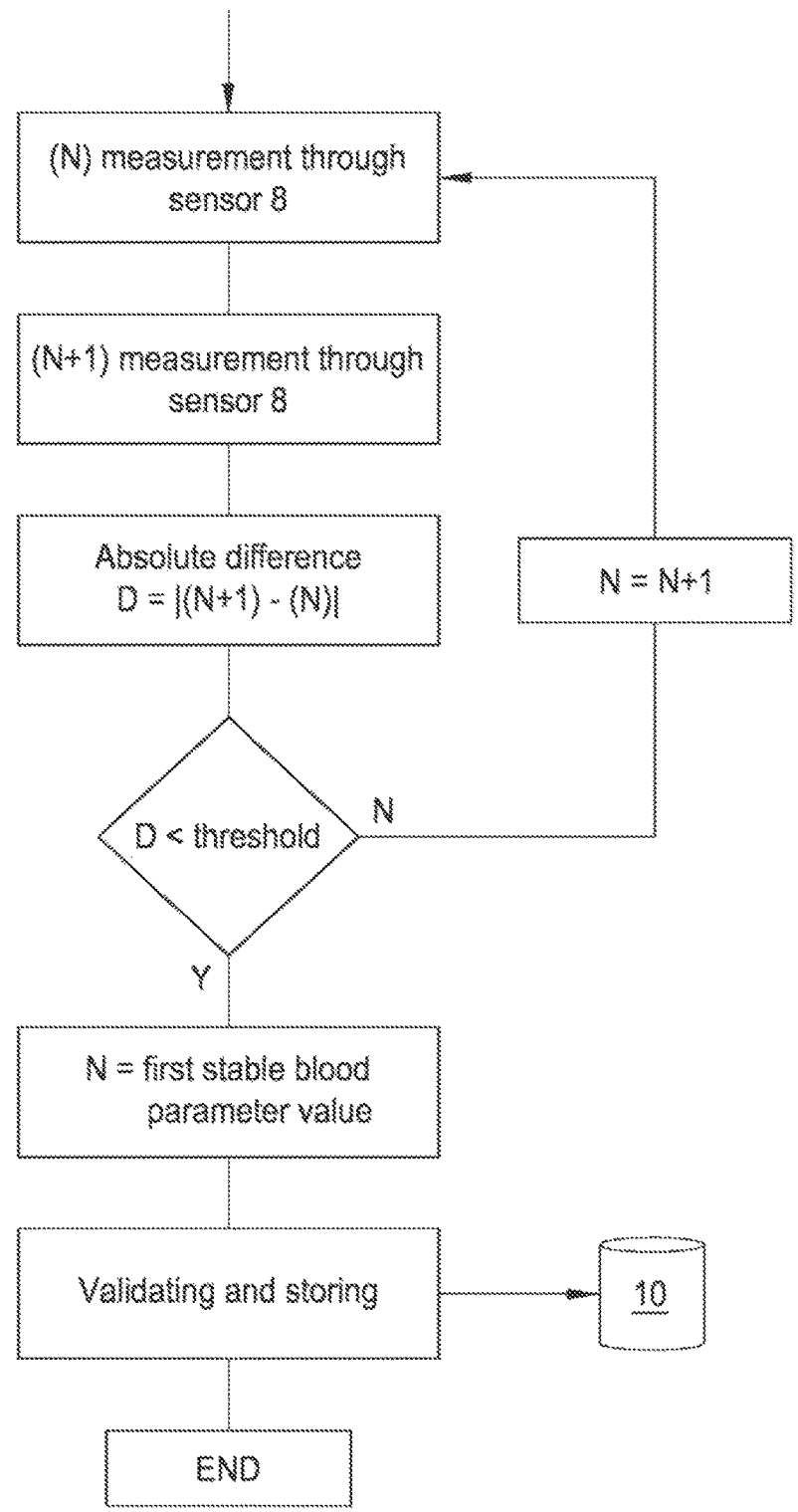

FIG. 7 shows the flow chart of an example of the validating process.

In particular the control unit obtains at least a first (N) and a second measure (N+1) of the blood parameter and a difference [D=(N+1)−(N)] between such values is determined.

If the absolute value of the difference is below a certain threshold (which might be 0.2 g/dl for example) then the measure is validated.

Otherwise the routine is repeated: the second measure is considered as the first measure (N=N+1) and a third one is made making the difference between the second and the third measure and reiterating the process till the difference is below the above mentioned threshold.

Once the condition is met, the first measure is considered as the first stable measured blood parameter value and it is stored in the storage memory 10.

Of course the process could be further improved by using more than two measurements to be checked.

By way of example a difference between the first and the second and the first and the third measurements could be made (as well as a difference between the first and the second and the second and the third measurements) checking thereafter whether the differences are below the above mentioned threshold or not.

Coming back to the example shown in FIG. 9, it is clear that the difference from the first aberrant value and second (reliable) measurements will be above the threshold and therefore value 7.1 will not be stored.

Vice versa the difference between the second and the third measurement (which is 0) will lead to the storing of the second measurement made (12.4) as the first stable blood parameter value.

It is clear that in the embodiment shown in FIG. 1, all the patient undergoing dialysis treatment on the single machine 2 of the medical apparatus will allow storing of the first stable parameter value in the internal storage memory 10.

By contrast the embodiment disclosed in FIG. 2 allows each first stable blood parameter value measured by anyone of the machine 2 to be stored in storage memory 10.

In this respect it is to be noted that the various blood treatment machines 2 could be connected in a network 44, such as a local network or even the internet, to server 42 and/or to storage memory 10.

Of course the network connection could be continuous over time (for example an internet connection always on) or could be discrete at determined time intervals (for example once per day).

On any case after several treatment sessions, the storage memory 10 will include a number of data, such as for example those shown in FIG. 11 and including in particular a timing (for example the day in which the value has been taken), a patient number or reference to univocally identify the patient, the sensor measured blood parameter value and, if present, the laboratory measured blood parameter value.

Even if it has been highlighted that the pre-dialytic first stable measured blood parameter value (non-limiting example) allows obtaining good results in terms of reliability of the method, also the end session value or the mean value of the sensor blood parameter measurement could be alternatively or in combination stored in the storage memory and used.

The control unit 9 is configured for taking from the storage memory 10 a plurality of measures related to the blood parameter value selecting, among all, the measure relating to the same patient and obtained during the various dialytic sessions the patent underwent.

Moreover the control unit 9 has at least an actual control value of the same blood parameter relating to the same patient.

Said actual control value is generally the laboratory measured value taking at certain time intervals (for example once per month, once every two weeks) or in any case a direct measure of the parameter.

Using a prefixed number of measures (all relating to die same patient) taken through the sensors 8 and the actual control value of the blood parameter obtained through the laboratory, the control unit is capable of determining a correcting factor.

A correcting factor allows obtaining an actual real value of the blood parameter when used in combination with at least the last measure made through the sensor 8.

Therefore the control unit 9 may be configured for obtaining value of the blood parameter by varying at least the last measure made through the sensor by means of the correcting factor.

Figure 6:
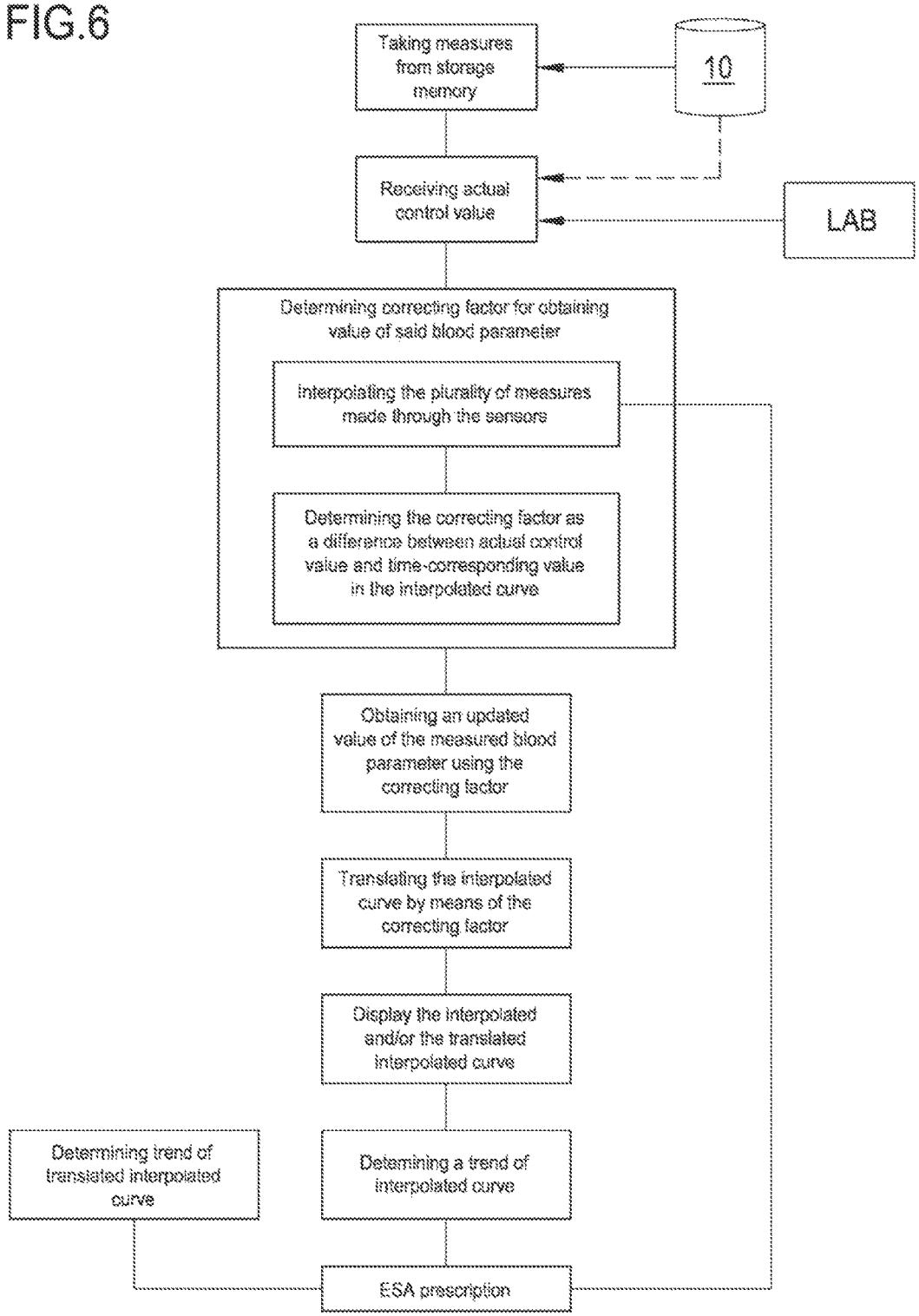

FIG. 6 illustrates a flow chart of the current here-below described method.

After taking the measures from the storage memory 10 and receiving form the input device 11 (e.g. storage memory 10 or the laboratory) the actual control value (please note that the above mentioned steps could be made at the same instant or reversed in sequence) the control unit 9 determines the correcting factor.

It is also to be noted that the laboratory value or the actual control value could be as well potted in the same storage memory 10 or in a different memory and then the control unit 9 can access such kind of value.

In other terms again the input device could be an automatic input device which directly (from a measurement made in a laboratory) could forward (without the operator intervention) such a value to a proper storage memory, for example storage memory 10 or to the control unit 9, upon request.

The calculation of the correcting factor may require the interpolation of the plurality of measures made through the sensor 8 for obtaining an interpolated curve 12 which defines a blood parameter trend along time.

Please note that such interpolated curve 12 could be displayed or not on a proper user interface.

Then the correcting factor may be determined as a difference between the actual control value (for example coming from the laboratory) and the time-corresponding value of the blood parameter in the interpolated curve.

As per time-corresponding value of the blood parameter in the interpolated curve, it is intended (at least) either a measure made at the time immediately preceding monitoring time, or a measured value at a time immediately following the monitoring time, or as interpolated value at a time equal to the monitoring time.

Figure 8:
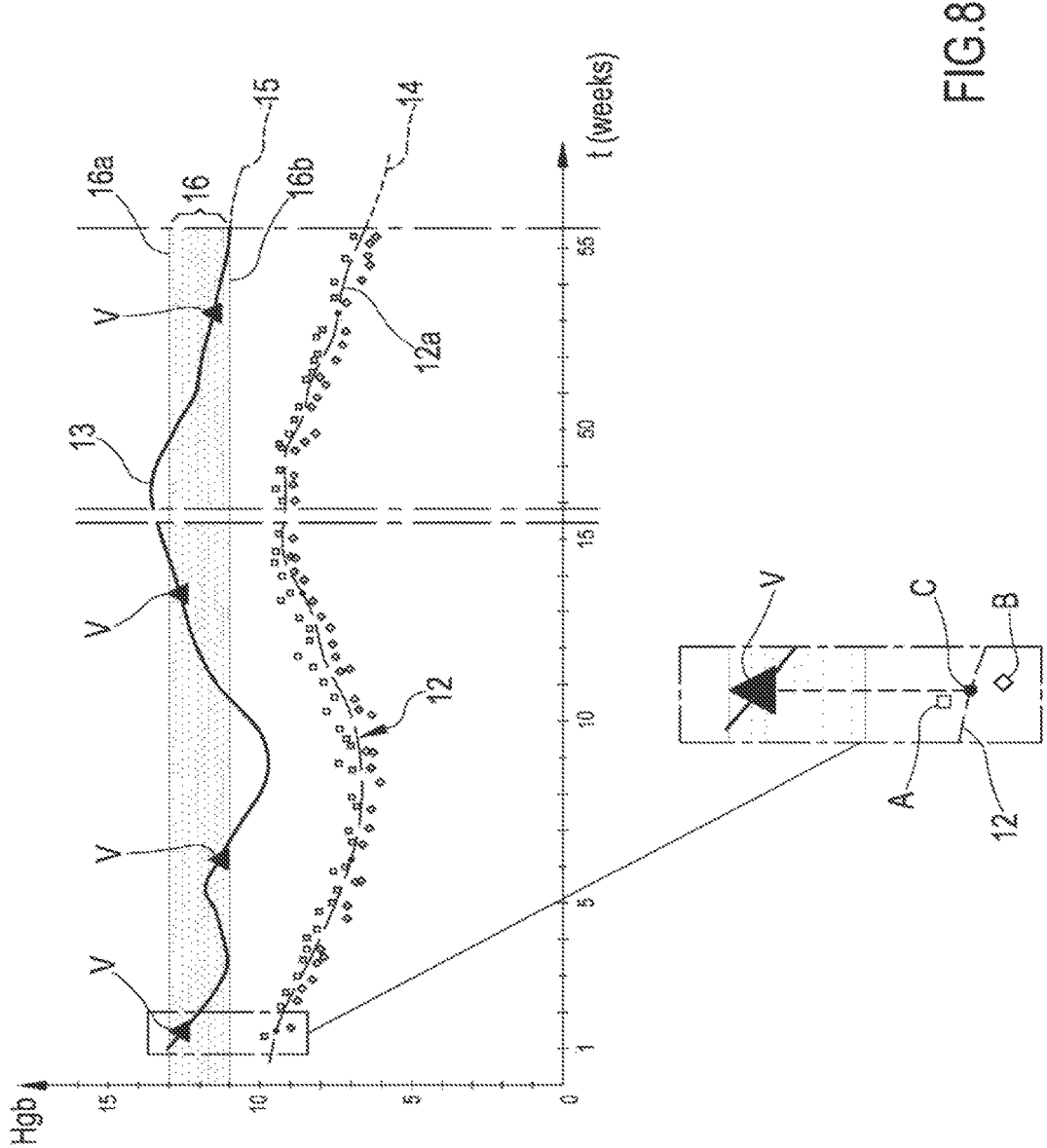

The diagram of the example of FIG. 8 illustrates is a schematic way the hemoglobin variation along time (time is shown as weeks, but days or hours or months can be used as time scale).

Referring to the portion of the diagram, the interpolated curve 12 is shown as an interrupted line and the actual control value V is obtained at the timing there between two successive sensor measurements.

The time-corresponding value of the blood parameter in the interpolated curve could be a previously measured value A, a successive measured value B or exactly the interpolated value C (value never measured, but only calculated) at a time equal to the monitoring time.

Of course if the laboratory measurement is made in correspondence of a dialysis session (as it often happens) the time-corresponding value of the blood parameter in the interpolated curve 12 might be directly the measured value of the blood parameter at a time equal to the monitoring time.

It is also clear that the interpolated curve 12 will not be in general coincident with the measured value and therefore the time-corresponding value, even in a situation on which on the same time is obtained a laboratory measurement and a sensor measurement, could be either the sensor measurement value or the fictitious interpolated value.

The control unit 9 is further configured for translating at least the last past 12a of the interpolated curve 12 using a correcting factor.

In general the last part 12a of the interpolated curve 12 comprises at least the last two (and generally a plurality) measured blood parameter values.

In general the user interface can display either last part of the translated interpolated curve 13 (or in general all the translated interpolated curve) or the at least test two (or plurality) translated blood parameter values.

The interpolated curve 12 or the translated, interpolated curve 13 (being substantially coincident apart for a shifting of a value equal to the correcting factor) allows determining a future trend 14, 15 of the curves themselves.

The future trend 14, 15 allows for predicting a blood parameter variation after a predetermined time interval.

In other terms having interpolated the curve it is possible to predict a future variation of the blood parameter after a certain time interval.

It is clear that the possibility of predicting such a variation allows the nephrologists to intervene on the patient through, for example drugs, in order to avoid or correct dangerous situations (not yet happened).

In case of monitoring the hemoglobin concentration, the physician can determine an erythropoietin stimulating agent prescription as a function of the translated blood parameter values or as a function of the predicted blood parameter variations so as to substantially maintain the hemoglobin content in the patient within an acceptable range 16 of the established hemoglobin values 16a, 16b.

As above mentioned the range could be in particular comprised between 11 and 13 g/dl.

Moreover, a part from helping the physician to prescribe the ESA, the described medical apparatus may allow to store and display for each patient a corrected real and actual trend of the hemoglobin, concentration, thereby allowing to show effectiveness and correctness of the treatment, for example, inside a clinic or inside an hospital using simple sensors and instruments yet present or easily added to the existing dialysis machine.

The regular surveillance of a biological parameter of the patient blood may be therefore obtained by a combined processing of a direct measure that is the best standard, achieved at long interval period, and an indirect measure of the same parameter available more frequently. Indirect measure may not be (and generally it is not) equal to direct measure, but direct measure can be derived from indirect measure.

Using a data base containing a series of recent recordings of indirect measures and direct measure, and also may be other parameters involved in the relationship between indirect measure and direct measure may be possible to figure out a mathematical relationship between indirect measures and direct measures and subsequently to extrapolate direct measures from indirect measures at any time whatever the factor of discrepancy between direct measure and indirect measure patient related, sensor related or time related.

As stated it is possible to extend the method to several other parameters in terms of blood indirect measurements vs direct measurements, such as conductivity vs sodium, and dialysance vs clearance, for instance.

The invention claimed is:

1. A medical apparatus (1) comprising:
at least one machine (2) for extracorporeal blood treatment having:
at least a blood treatment unit (3);
an extracorporeal blood line (4) having a withdrawal branch (5) adapted to withdraw blood from a patient access (6) of a patient and to bring the withdrawn blood to the blood treatment unit (3) and a return branch (7) adapted to bring the blood from the blood treatment unit (3) to the patient; and
at least one hematocrit sensor (8) associated to the extracorporeal line (4) and to provide a measure of a hemoglobin value of the blood of the patient circulating in the extracorporeal blood line (4);
a control unit (9); and
at least one storage memory (10) for storing measures of the hemoglobin value, each measure being made through one of the at least one hematocrit sensor (8) of said machine (2) and each measure corresponding to different treatment sessions of patients on said machine (2);
the control unit (9) being configured for performing the following steps:
taking from the at least one storage memory (10) a plurality of measures of the hemoglobin value, said plurality of measures of the hemoglobin value relating to a same patient;
receiving at least an actual control hemoglobin value relating to the same patient, said actual control hemoglobin value being measured at a monitoring time, said actual control hemoglobin value being a real absolute value of hemoglobin of the blood of the same patient measured through laboratory measurements;
determining a correcting factor as a difference between a time-corresponding measure of the hemoglobin value of the plurality of measures of the hemoglobin value relating to the same patient corresponding to the monitoring time and the actual control hemoglobin value;
obtaining an actual hemoglobin value by correcting at least a last measure of the hemoglobin value made through the at least one hematocrit sensor by means of the correcting factor; and
determining an erythropoietin stimulating agent prescription based on at least the plurality of measures of the hemoglobin value and the correcting factor.

2. The medical apparatus according to claim 1, wherein the control unit (9) is configured for performing the following steps:
interpolating said plurality of measures of the hemoglobin value made through the at least one hematocrit sensor (8) for obtaining an interpolated hemoglobin curve (12) defining a hemoglobin trend along time; and
determining the correcting factor as a difference between the actual control hemoglobin value and a time-corresponding hemoglobin value in the interpolated hemoglobin curve.

3. The medical apparatus according to claim 2, wherein the control unit (9) is further configured for performing the following steps:
shifting at least a last part (12a) of the interpolated hemoglobin curve (12) based on the correcting factor, the last part (12a) of the interpolated hemoglobin curve (12) comprising at least a last two measures of hemoglobin value; and
displaying either the at least the last part of the shifted interpolated hemoglobin curve (13) or the last two measures of hemoglobin value.

4. The medical apparatus according to claim 3, wherein the control unit (9) is further configured for determining either a future trend (14) of the shifted interpolated curve (12) or a future trend (15) of the shifted interpolated curve for predicting a hemoglobin variation after a predetermined time interval.

5. The medical apparatus according to claim 2, wherein the control unit (9) is further configured for determining the erythropoietin stimulating agent prescription as a function of the interpolated hemoglobin curve (12) and the correcting factor.

6. The medical apparatus according to claim 3, wherein the control unit (9) is further configured for determining the erythropoietin stimulating agent prescription as a function of the shifted hemoglobin values.

7. The medical apparatus according to claim 4, wherein the control unit (9) is further configured for determining the erythropoietin stimulating agent prescription as a function of the predicted hemoglobin variation.

8. The medical apparatus according to claim 5, wherein the control unit (9) determines said erythropoietin stimulating agent prescription to maintain the hemoglobin value in a range (16) of established hemoglobin values (16a, 16b), said range being in particular comprised between 11 and 13 g/dl.

9. The medical apparatus according to claim 1, wherein each at least one machine (2) includes a processor (19) configured for:
validating a first stable measure of hemoglobin value in a single treatment session; and
storing said validated first stable measure of hemoglobin value in the storage memory (10) together with time information and a patient identification data.

10. The medical apparatus according to claim 9, wherein the processor (19) is configured for validating the first stable measure of hemoglobin value in the single treatment session by:
obtaining at least a first measure of hemoglobin value and a second of hemoglobin value, and optionally a third measure of the hemoglobin value;
determining a difference between the first measure of hemoglobin value and the second measure of hemoglobin value, and optionally between the first measure of hemoglobin value and the third measure of hemoglobin value or the second measure of hemoglobin value and the third measure of hemoglobin value;
comparing said difference with a prefixed threshold; and
validating the first stable measure of hemoglobin value if an absolute value of the difference is below said prefixed threshold.

11. The medical apparatus according to claim 1, wherein the at least one hematocrit sensor (8) comprises at least an emitter (17) of an ondulatory signal and a receiver (18) of the ondulatory signal, the emitted ondulatory signal crossing at least part of the extracorporeal blood line (4) and being partly absorbed and partly scattered by the blood inside the extracorporeal blood line, the at least one hematocrit sensor comprising an optical sensor, the apparatus also comprising a processor (19) determining the measures of hemoglobin value as a function of the ondulatory signal received by the receiver.

12. The medical apparatus according to claim 11, wherein the at least one hematocrit sensor (8) further comprises a rigid tubular element (20) interposed between two consecutive, flexible, tubings (21, 22) of the withdrawal branch (5) of the extracorporeal blood line (4), the emitter (17) and the receiver (18) being placed on opposite sides of said rigid tubular element (20) with respect to a blood flow direction (23), the rigid tubular element (20) being at least partly transparent to the ondulatory signal emitted by the emitter (17).

13. The medical apparatus according to claim 12, wherein said rigid tubular element (20) has a measurement portion (24) exhibiting a constant, circular cross-section.

14. The medical apparatus according to claim 11, wherein the at least one hematocrit sensor (8) further comprises at least one mirror (25) placed between the emitter (17) and the receiver (18) and outside the extracorporeal blood line (4) for reflecting at least the scattered part of the ondulatory signal.

15. The medical apparatus according to claim 1, the at least one hematocrit sensor (8) providing different measures of hemoglobin value for different patients having the same actual hemoglobin value.

16. The medical apparatus according to claim 1, further comprising an input device (11) for providing the control unit (9) with at least the actual control hemoglobin value, said input device (11) being chosen in a group comprising: a manual input or an automatic input device, said automatic input device including a remote processing unit (43) having the actual control hemoglobin value and sending the actual control hemoglobin value either to the storage memory (10) or to the control unit (9).

17. A controller for a medical apparatus (1), said medical apparatus comprising at least one machine (2) for extracorporeal blood treatment connectable to at least a blood treatment unit (3), to an extracorporeal blood line (4) having a withdrawal branch (5) adapted to withdraw blood from a patient access (6) and to bring the withdrawn blood to the blood treatment unit (3) and a return branch (7) adapted to bring the blood from the blood treatment unit (3) to the patient, and to at least one hematocrit sensor (8) associated to the extracorporeal line (4) and to provide a measure of a hemoglobin value of the blood circulating in the extracorporeal blood line (4), the medical apparatus including at least one storage memory (10) for storing measures of the hemoglobin value, each measure of the hemoglobin value being made through one of the at least one hematocrit sensor (8) of said machine (2) and each measure of the hemoglobin value corresponding to different treatment sessions of patients on said machine (2), the controller being configured for performing the following steps:

taking from the at least one storage memory (10) a plurality of measures of the hemoglobin value, said plurality of measures of the hemoglobin value relating to a same patient;

receiving at least an actual control hemoglobin value relating to the same patient, said actual control hemoglobin value being measured at a monitoring time, said actual control hemoglobin value being a real absolute value of hemoglobin of the blood of the same patent measured through laboratory measurements;

determining a correcting factor as a difference between a time-corresponding measure of the hemoglobin value of the plurality of measures of the hemoglobin value relating to the same patient corresponding to the monitoring time and the actual control hemoglobin value;

obtaining an actual hemoglobin value by correcting at least a last measure of the hemoglobin value made through the at least one hematocrit sensor by means of the correcting factor; and determining an erythropoietin stimulating agent prescription based on at least the plurality of measures of the hemoglobin value and the correcting factor.

18. A method for prescribing an erythropoietin stimulating agent in a medical apparatus for the extracorporeal blood treatment comprising:

a prefixed number of machines (2) for extracorporeal blood treatment;

at least a blood treatment (3) unit;

an extracorporeal blood line (4) having a withdrawal branch (5) adapted to withdraw blood from a patient access (6) and to bring the withdrawn blood to the blood treatment unit (3) and a return branch (7) adapted to bring the blood from the blood treatment unit (3) to the patient;

at least one hematocrit sensor (8) associated to the extracorporeal line (4) and adapted to provide a measure of a hemoglobin value of the blood circulating in the extracorporeal blood line (4);

a control unit (9);

at least one storage memory (10) for storing measures of the hemoglobin value, each measure being made through one of the at least one hematocrit sensor (8) of said prefixed number of machines (2) and corresponding to different treatment sessions of patients on said prefixed number of machines;

an input device (11) for providing in the control unit (9) with at least an actual control hemoglobin value, the method comprising the step of taking from the storage memory (10) a plurality of measures of the hemoglobin value, each of the plurality of measures of the hemoglobin value relating to a same patient;

receiving at least an actual control hemoglobin value made at a monitoring time and relating to the same patient, said actual control hemoglobin value being a real absolute value of hemoglobin of the blood of the patent measured through laboratory measurements;

determining a correcting factor as a difference between a time-corresponding measure of the hemoglobin value of the plurality of measures of the hemoglobin value relating to the same patient corresponding to the monitoring time and the actual control hemoglobin value;

obtaining an actual hemoglobin value by correcting at least a last measure of the hemoglobin value made though the at least one hematocrit sensor by means of the correcting factor; and determining an erythropoietin stimulating agent prescription based on at least the plurality of measures of the hemoglobin value and the correcting factor.

19. A method according to claim 18, further comprising the steps of:

interpolating said plurality of measures of the hemoglobin value for obtaining an interpolated hemoglobin curve;

defining a hemoglobin trend along time; and determining the correcting factor as a difference between the actual control hemoglobin value and a time-corresponding value of hemoglobin in the interpolated hemoglobin curve.

20. A method according to claim 19, comprising the step of determining an erythropoietin stimulation agent prescription as a function of the interpolated hemoglobin curve (12).

21. A method according to claim 20, comprising the step of determining an erythropoietin stimulating agent prescription as a function of a predicted hemoglobin variation, said predicted hemoglobin variation being obtained through a step of determining a future trend (14) of the interpolated hemoglobin curve (12) or determining a future trend (15) of a translated interpolated hemoglobin curve for predicting the hemoglobin variation after a predetermined time interval.

22. A method according to claim 19, wherein the time-corresponding value of hemoglobin in the interpolated hemoglobin curve is chosen between: a measured hemoglobin value at a time immediately preceding the monitoring time, a measured hemoglobin value at a time immediately following the monitoring time, and a measured hemoglobin value at a time substantially corresponding to an interpolated value at a time equal to the monitoring time.

23. A method according to claim 19, comprising the steps of:
    shifting at least a last part (12a) of the interpolated hemoglobin curve (12) by means of the correcting factor, the last part (12a) of the interpolated hemoglobin curve (12) comprising at least a last two measures of hemoglobin value; and
    displaying either the shifted interpolated hemoglobin curve (13) or the last two measures of hemoglobin value.

24. A method according to claim 20, wherein said erythropoietin stimulating agent prescription is determined to maintain the actual hemoglobin value within a range (16) of established hemoglobin values (16a, 16b), said range being in detail comprised between 11 and 13 g/dl.

25. A method according to claim 18, further comprising the steps of:
    validating a first stable measure of hemoglobin value in a single treatment session; and
    storing said validated first stable measure of hemoglobin value in the storage memory (10) together with time information and a patient identification data.

26. A method according to claim 25, wherein the step of validating is performed by:
    obtaining at least a first measure of hemoglobin value and second measure of hemoglobin value, and optionally a third measure of the hemoglobin value;
    determining a difference between the first measure of hemoglobin value and the second measure of hemoglobin value, and optionally between the first and the third measure of hemoglobin value or second and third measure of hemoglobin value;
    comparing an absolute value of said difference with a prefixed threshold;
    validating the first stable measure of hemoglobin value if the absolute value of the difference is below said prefixed threshold.

* * * * *